United States Patent [19]

Kiener

[11] Patent Number: 5,236,832
[45] Date of Patent: Aug. 17, 1993

[54] MICROBIOLOGICAL OXIDATION OF METHYL GROUPS IN HETEROCYCLES

[75] Inventor: Andreas Kiener, Visp, Switzerland

[73] Assignee: Lonza, Ltd., Campel/Valais, Switzerland

[21] Appl. No.: 784,704

[22] Filed: Oct. 30, 1991

Related U.S. Application Data

[63] Continuation of Ser. No. 650,589, Feb. 5, 1991, Pat. No. 5,104,798.

[30] Foreign Application Priority Data

Feb. 13, 1990 [CH] Switzerland .................... 458/90

[51] Int. Cl.⁵ .................. C12P 17/00; C12P 17/10; C12P 17/04; C12R 1/40
[52] U.S. Cl. ........................... 435/117; 435/118; 435/119; 435/120; 435/121; 435/122; 435/123; 435/124; 435/125; 435/126; 435/253.3; 435/877
[58] Field of Search ............... 435/117, 118, 119, 120, 435/121, 122, 123, 124, 125, 126, 253.3, 877

[56] References Cited

U.S. PATENT DOCUMENTS

| | | | |
|---|---|---|---|
| 3,393,289 | 7/1968 | Duhamel et al. | 219/121 |
| 4,859,592 | 8/1989 | Hagedorn et al. | 435/122 |
| 5,104,798 | 4/1992 | Kiener | 435/117 |

FOREIGN PATENT DOCUMENTS

| | | |
|---|---|---|
| 0233656 | 3/1987 | European Pat. Off. |
| 228688 | 2/1969 | U.S.S.R. |
| 302341 | 4/1971 | U.S.S.R. |
| 417468 | 7/1974 | U.S.S.R. |

OTHER PUBLICATIONS

Ullman, vol. 19, (1980), p. 603.
Ullman, vol. 23 (1980), p. 146.
Ullman, vol. 23, (1980), p. 216.
Raymond et al., Process Biochem., (1969), pp. 71 to 74.
Abril, M.-A., et al., J. Bacteriol., vol. 171, (1989), pp. 6782 to 6789.
Burlage et al., Appl. Environ. Microbiol., 55 (1989), pp. 1323 to 1328.
Harayama et al., J. Bacteriol., 171, (1989), pp. 5048 to 5055.
Kulla et al., Arch., Microbiol., 135, (1983), pp. 1 to 7.
Claus et al., Jr. Gen. Microbiol., 36, (1964), pp. 107 to 122.
Roemps Chemie Lexikon, vol. 5, (1987), p. 3411.
Soviet Inventions Illustrated, Chemical Section, Week Y08 (Apr. 5, 1977), Derwent Publ., D15, p. 2, Abs: 14207Y/08.
Soviet Inventions Illustrated, Chemical Section, Week U44, vol. V No. 44, (Dec. 12, 1973), Derwent Publ., D16–E14, p. 4.
Soviet Inventions Illustrated, Chemical Section, Week W2, vol. W No. 2, (Feb. 18, 1975), Derwent Publ., D16–E13, p. 1.
Soviet Inventions Illustrated, Chemical Section, (May 1969), Derwent Publ., p. 3 (Jun. 1969).

*Primary Examiner*—Herbert J. Lilling
*Attorney, Agent, or Firm*—Fisher, Christen & Sabol

[57] ABSTRACT

A microbiological process for the oxidation of methyl groups in aromatic 5- or 6-member ring heterocycles to the corresponding carboxylic acid. The heterocycle serves as the substrate and exhibits no substituent on the carbon atoms adjacent to the methyl groups to be oxidized. The reaction of the heterocycle takes place by means of microorganisms of the genus Pseudomonas utilizing toluene, xylene, or cymene. The enzymes of the microorganisms been previously induced.

19 Claims, 1 Drawing Sheet

MICROBIOLOGICAL OXIDATION OF METHYL GROUPS IN HETEROCYCLES

This is a continuation of application Ser. No. 650,589, filed on Feb. 5, 1991, now U.S. Pat. No. 5,104,798, of Andreas Kiener, for MICROBIOLOGICAL OXIDATION OF METHYL GROUPS IN HETEROCYCLES.

BACKGROUND OF THE INVENTION

1. Field Of The Invention

The invention relates to a new microbiological process for oxidation of methyl groups in aromatic 5- or 6-member ring heterocycles to the corresponding carboxylic acid. The heterocycle has no substituent on the carbon tom adjacent to the methyl group to be oxidized. The heterocycle serves as substrate for the reaction which is performed by microorganisms of the genus Pseudomonas utilizing toluene, xylene or cymene, whose enzymes were previously induced.

2. Background Art

These heterocyclic carboxylic acids, for example, are important intermediate products for the product of pharmaceutical agents. For example, nicotinic acid (3-pyridine carboxylic acid) is an important intermediate product for the production of nicotinic acid amide, which represents a vitamin of the B group and has an essential importance for the nutrition of men and animals [Ullmann, Vol. 19, (1980), p. 603]. 2-Pyrazine carboxylic acid, e.g., is an important intermediate product for the production of the tuberculostatic agent pyrazinamide (2-pyrazine carboxylic acid amide), [Roemos Chemie Lexikon, Vol. 5, (1987),3411]. 4-Thiazole carboxylic acid serves for the production of thiabendazol, a highly effective antihelminthic (helminthicide), which in turn is a starting material for other newer antihelminthic agents, such as, cambendazole [Ullmann. Vol. 23, (1980), p. 46]. 2-Thiophene carboxylic acid has an antiallergic effect [Ullmann, Vol. 23, (1980), p. 219].

In-depth investigations for the oxidation of methyl groups so far have been conducted with aromatic hydrocarbons.

The production of carboxylic acids by the microbial oxidation of methylated aromatic compounds was exhaustively described in the works of Raymond et al. [Raymond et al., Process Biochem., (1969), pp. 71 to 74]. U.S. Pat. No. 3,393,289 describes a process for the biochemical oxidation of methyl groups in aromatic hydrocarbons with a gram-positive microorganism strain of the genus Nocardia. Drawbacks of these processes are that, for example, in the methyl group oxidation of aromatic hydrocarbons the benzene ring of the corresponding acid is cleaved off.

In regards to the use of Pseudomonas putida ATCC 33015, it is known that the biochemical oxidation of the methyl group from toluene to benzoic acid takes place in three steps. By the action of toluene monoxygenase first benzyl alcohol results, which then in two other steps, catalyzed by an alcohol dehydrogenase and aldehyde dehydrogenase, is reacted to the acid. In this strain, both the Xyl gene, which codes for enzymes of the xylene degradation, and the genes, which are responsible for the regulation of the Xyl gene, lie on the plasmid pWWO. This archetypal Tol plasmid has already been thoroughly studied in a molecular biological manner [Harayama et al., J. Bacteriol. 171, 1989), pp. 5048 to 5055; Burlage et al., Appl. Environ Microbiol. 55, (1989), pp. 1323 to 1328].

Likewise, microbiological processes for the oxidation of methyl groups of an N-heterocycle are also known from the literature. According to Soviet Union Pat. No. 417,468, 2-methyl pyridine is oxidized with a gram-positive microorganism strain of the genus Nocardia to the corresponding acid.

Soviet Union Pat. No. 228,688 describes a microbiological process for the production of nicotinic acid from 3-methyl pyridine with a gram-positive microorganism of the genus Mycobacterium. A microbiological process for the production of nicotinic acid with gram-positive bacteria of the genus Nocardia is known from Soviet Union Pat. No. 302,341.

The drawbacks of the methyl groups oxidation of N-heterocycles with gram-positive bacteria are that, with such alkane-utilizing bacteria the mixture ratio of the alkane to the substance to be oxidized has to be adjusted exactly to achieve a biotransformation and that no biotransformation of the substrate occurs in the absence of the alkane, i.e., the alkane used for the induction, always has to be present, also in the reaction of the substrate. By comparative tests with the gram-positive bacterium Nocardia and applicants' gram-negative Pseudomonas, it was clearly shown that using Nocardia even in the presence of an alkane, such as, dodecane, 3-methyl pyridine could not be oxidized to nicotinic acid.

In addition, U.S. Pat. No. 4,859,592 described a process for the production of picolinic acid with Pseudomonas putida by an alkyl-substituted aromatic hydrocarbon being formed in the presence of molecular oxygen in a first step by a dioxygenase into a 2-hydroxy muconic acid semialdehyde, and then the latter being reacted in a second step with ammonia or a primary amine to 2-picolinic acid. The drawback of such process is that the corresponding picolinic acid is formed only in the second step by the reaction of the 2-hydroxy muconic acid semialdehyde with ammonia.

BROAD DESCRIPTION OF THE INVENTION

An object of the invention is to in eliminate the above-described prior art drawbacks and to develop a simple and one-step process for the microbiological methyl group oxidation with which the corresponding acids can be isolated in good yield and purity and the aromatic heterocycle is not cleaved off. A further object is to make available a process in which the compound used for the induction, after completion of the induction of the enzyme, no longer has to be present during the reaction of the substrate and, thus, the reaction does not depend on the amount of the enzyme inducer.

The objects of the process are achieved by the process of the invention. The invention process is a microbiological process for oxidation of methyl groups in aromatic 5- or 6-member ring heterocycles. The heterocycle exhibits no substituent on the carbon atom adjacent to the methyl group to be oxidized to the corresponding carboxylic acid. The methylated heterocycle is used as substrate for the reaction. The reaction is performed by microorganisms of the genus Pseudomonas, utilizing toluene, . xylene or cymene, whose enzymes were previously induced.

DETAILED DESCRIPTION OF THE INVENTION

Figure 1:
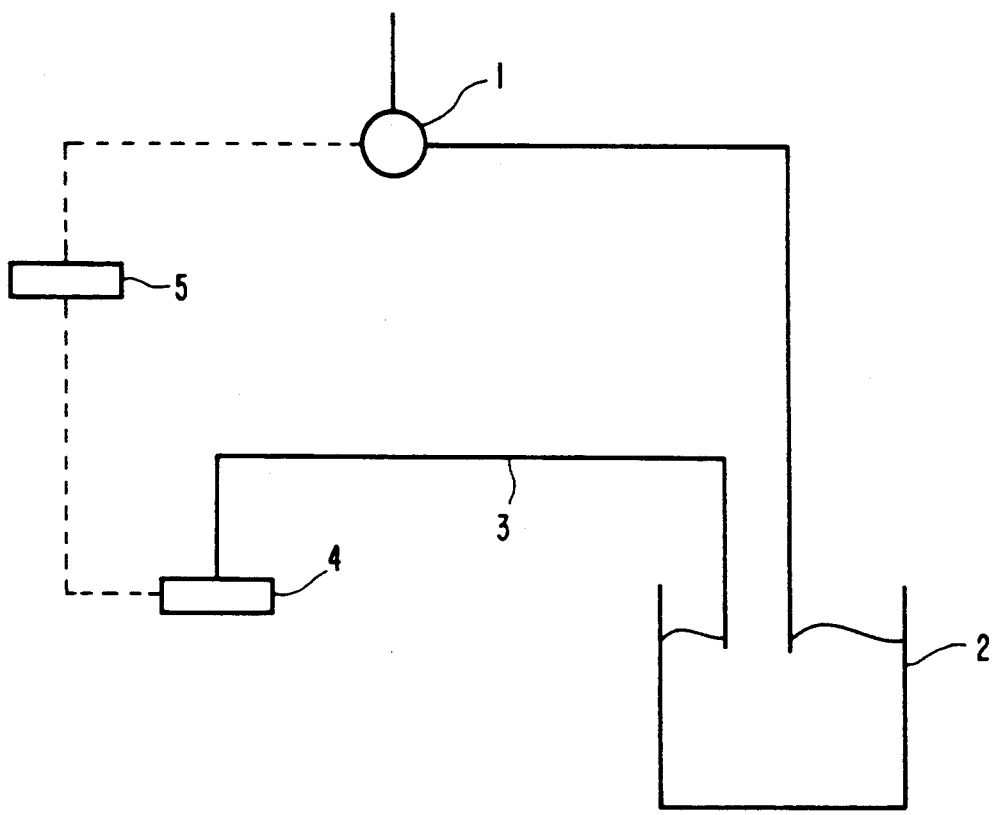
FIG. 1 is a schematic diagram of the equipment used in a preferred embodiment of the invention.

The reaction is suitably performed by microorganisms of the species *Pseudomonas putida* utilizing toluene, xylene or cymene.

Preferably the xylene-utilizing microorganism strain *Pseudomonas putida* with the designation ATCC 33015 or an effective mutant of the latter or the cymene-utilizing microorganism strain Pseudomonas putida with the designation DSM 5709 or an effective mutant of the latter is used. The reaction is performed especially with the microorganism strain *Pseudomonas putida* ATCC 33015. The microorganism strain *Pseudomonas putida* (DSM 5709) was deposited with the German Collection of Microorganisms (DSM) and Zellkulturen [Cell Cultures] GmbH, Mascheroderweg 1b, 3300 Braunschweig, FRG, on Dec. 12, 1989 under number DSM 5709.

The microorganism strain *Pseudomonas putida* with the designation ATCC 33015 was deposited with the American Type Culture Collection, 12301 Parklawn Drive, Rockville, Maryland 20852, U.S.A., under number ATCC 33015.

The enzyme induction can suitably be performed both with compounds, which serve the microorganism as carbon source and energy source, such as, p-xylene, m-xylene, p-cymene, m-cymene and toluene, and with compounds, which do not serve the microorganism as carbon source and energy source, such as, monosubstituted and disubstituted methyl toluenes, ethyl toluenes and chlorotoluenes, benzyl alcohols and p-chlorobenzaldehyde, which have already been described as enzyme inducers for the degradation of aromatic hydrocarbons [Abril, M.-A., et al., J. Bacteriol., Vol. 171, (1989), pp. 6782 to 6789]. Preferably the enzyme induction is performed with p-xylene, m-xylene, 2-chlorotoluene or 2-bromotoluene.

The compounds utilized for induction can either be present during the reaction of the substrate or their feeding can be stopped before the reaction of the substrate. The inducer concentration is usually selected so that it is lower than the minimal inhibitory concentration of the enzymes responsible for the reaction. Depending on the embodiment of the process, preferably the addition of the compounds used for the induction is stopped during the reaction of the substrate either by stopping the feeding or by centrifuging off of the cells.

The strains used in the invention usually grow with p-xylene, m-xylene, p-cymene, m-cymene or toluene as the sole carbon source and energy source in a mineral medium [Kulla et al., Arch. Microbiol., 135, (1983), pp. 1 to 7] or in a complex medium ("Nutrient Broth Nr. 2", Oxoid Ltd., G.B.) or in a minimal medium, whose composition is indicated in Table 3. The growth substrate was fed to the medium in gaseous form according to the data of Claus and Walker [J. Gen. Microbiol., 36, (1964), pp. 107 to 122], and the gassing rate was 0.5 V/min.

Before the substrate addition, the cells are cultured to an optical density of 1 to 200 at 650 nm in the culture medium, preferably up to an optical density of 5 to 100 at 650 nm.

The reaction can suitably take place either with a single or continuous substrate addition so that the substrate concentration in the culture medium does not exceed 20 percent (w/v). Preferably the substrate addition takes place so that the substrate concentration in the culture medium does not exceed 5 percent (w/v). Depending on the embodiment, the substrate addition can also take place at the same time as the enzyme inducer, for example, by a mixture of enzyme inducer and substrate being used.

The reaction is suitably performed in a pH range of 4 to 11, preferably from 6 to 10. Suitably the reaction is usually performed at a temperature of 15° to 50° C., preferably at a temperature of 25° to 40° C. The reaction is usually performed in a period of 1 to 24 hours.

As substrates for the reaction methylated aromatic 5-member ring heterocycles can suitably be used, which contain one or more heteroatoms from the series of oxygen, nitrogen and sulfur, such as, methylated thiophenes, methylated furans, methylated pyrroles, methyated thiazoles, methylated pyrazoles or methylated imidazoles, which exhibit no substituent on the carbon atom adjacent to the methyl group to be oxidized. Preferably methylated furan, methylated thiophenes, methylated pyrroles and methylated thiazoles are used. 3,5-dimethylpyrazole, 5-methylthiazole, 4-methylthiazole, 2,5-dimethylthiophene, 2-methylthiophene, 3-methylthiophene, 2,5-dimethylfuran and 2,5-dimethylpyrrole are especially used as 5-member ring heterocycles.

The reaction can be suitably performed with aromatic methylated 6-member ring heterocycles with one or more nitrogen atoms as heteroatom, such as, methylated pyridines, methylated pyrimidines, methylated pyrazines or methylated pyridazines, which exhibit no substituent on the carbon atoms adjacent to the methyl groups to be oxidized. Preferably methylated pyridines, methylated pyrazines and methylated pyrimidines, such as, 2-methylpyridine, 3-methylpyridine, 4-methylpyridine, 2,5-dimethylpyridine, 2,4-dimethylpyridine, 6-chloro-3-methylpyridine, 2-chloro-3-ethyl-6-methylpyridine, 4,6-dimethylpyrimidie, 2-methylpyrazine, 2,5-dimethylpyrazine, 2-6-dimethylpyrazine, 2,3,5-trimethylpyrazine and 2-chloro-3,6-dimethylpyrazine, are used.

A preferred embodiment of the process is represented in FIG. 1. According to this embodiment, the enzyme inducer and/or the methylated heterocycle can be fed as substrate into a bioreactor (2), and the amount of feed is regulated by the concentration of the enzyme inducer in exhaust air (3) or bioreactor (2). Preferably the concentration of the enzyme inducer in exhaust air (3) is measured with a measuring device (4). As a measuring device for the enzyme inducer concentration, for example, a photometer for ultraviolet light, a gas chromatograph or a gas chromatograph coupled with a mass spectrometer can be used. This measuring device (4) is suitably coupled with control (5), which regulates the amount of feed of the enzyme inducer and/or of the methylated heterocycle with a pump (1), by which the feed of the enzyme inducer and/or of the methylated heterocycle takes place in bioreactor (2). The feeding of the enzyme inducer and/or of the methylated heterocycle is suitably regulated by this coupling. Preferably the concentration of the enzyme inducer in exhaust air (3) is kept constant by this regulation. The regulation suitably takes place so that the concentration of the enzyme inducer in exhaust air (3) is between 0.001 and 10 mmol/l of exhaust air, preferably between 0.01 and 3 mmol/l of exhaust air. Preferably the enzyme inducer and/or the methylated heterocycle is fed as substrate in the form of a mixture into bioreactor (2). The ratio of the enzyme inducer to substrate is suitably between 5:1 and 3:1. According to this embodiment, the enzyme inducer and/or the methylated heterocycle is suitably fed to bioreactor (2) by the incoming air.

Figure 2:
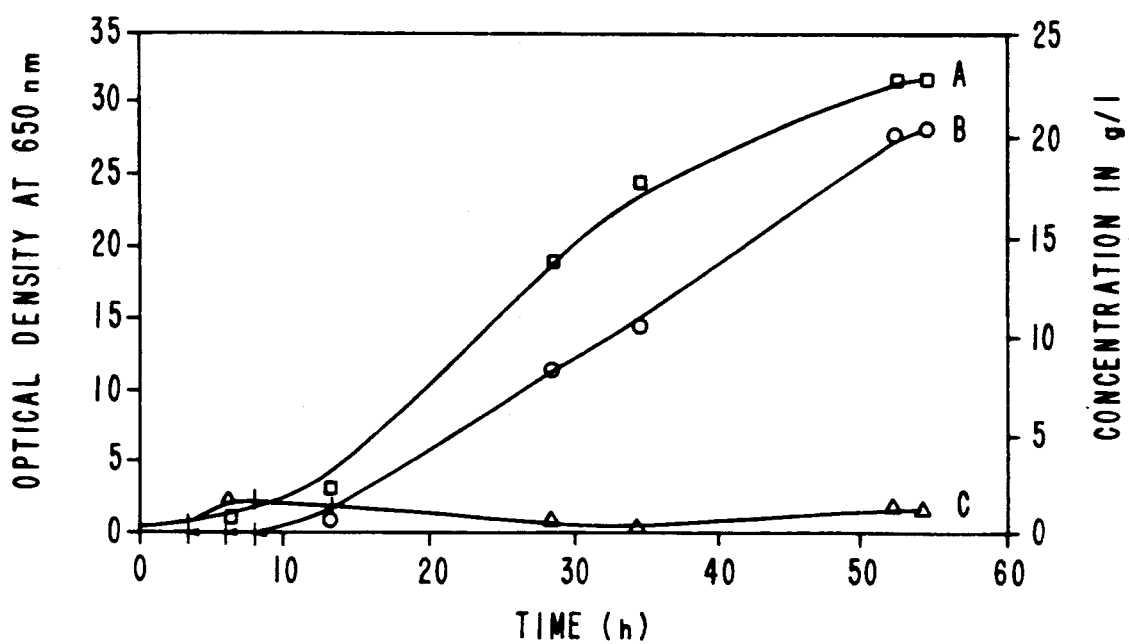
FIG. 2 is a graph which shows the results of the biotransformation in FIG. 1.

FIG. 2 shows the results of the biotransformation in the preferred embodiment.

After the reaction, the corresponding acids can be isolated in a known way, for example by extraction with organic solvent or, if the alkali salt of the heterocyclic carboxylic acid is formed, by concentration by evaporation of the cell-free culture medium. The alkali salt of the heterocyclic carboxylic acid can be formed, for example, by addition of an alkali hydroxide for adjustment of the pH of the culture medium.

According to the invention a simple and one-step microbiological process for the oxidation of methyl groups in aromatic 5- or 6-member ring heterocycles is made available with which the corresponding acids are isolated in good yield and purity. Another advantage of this process consists in the fact that the aromatic heterocycle is not cleaved off and the reaction rate does not depend on the amount of the enzyme inducer.

EXAMPLE 1

5-Methyl-2-Pyrazine Carboxylic Acid

*Pseudomonas putida* ATCC 33015 was cultured in a complex medium (100 ml) "Nutrient Broth Nr. 2" (Oxoid Ltd., England) in a fermenter at pH 7.0 and at a temperature of 30° C. The enzyme inducer p-xylene was fed in gaseous form according to the data of Claus and Walker [J. Gen. Microbiol., 36, (1964), pp. 107 to 122] up to a concentration of 1 mmol/liter. Then the cells were washed twice with mineral medium [Kulla et al., Arch. Microbiol., 135, (1983), pp. 1 to 7]and an optical density of 10 at 650 nm in 100 ml of mineral medium was set. 1 mmol of 2,5-dimethylpyrazine, which corresponds to a substrate concentration of 0.108 percent (w/v) in 100 ml, was added to this cell suspension. After an incubation of 4 hours at 30° C. there was obtained, in the absence of the enzyme inducer, 0.9 mmol of 5-methyl-2-pyrazine carboxylic acid corresponding to a yield of 90 percent, relative to the 2,5-dimethylpyrazine used.

EXAMPLE 2

Corresponding to Example 1, the following compounds were also used as enzyme inducer, which are summarized in table 1 with the corresponding concentration.

TABLE 1

| Enzyme inducer | Concentration [moles in 100 ml of cells] (mmol) | Substrate amount [1 mmol in 100 ml of cells corr. 0.108% (w/v)] | Percent Yield Of 5-methyl-2-pyrazine carboxylic acid |
|---|---|---|---|
| x-xylene | 0.1 | 2,5-dimethyl pyrazine | 90 |
| m-xylene | 0.1 | 2,5-dimethyl pyrazine | 90 |
| 2-chloro-toluene | 0.1 | 2,5-dimethyl pyrazine | 90 |
| 2-bromo-toluene | 0.1 | 2,5-dimethyl pyrazine | 90 |

EXAMPLE 3

5Methyl-2-Pyrazine Carboxylic Acid

*Pseudomonas putida* ATCC 33015 was cultured according to Example 1 but in mineral medium [Kulla et al., Arch. Microbiol., 135, (1983), pp. 1 to 7] with p-xylene as the sole carbon source and energy source. 1 mmol of 2,5-dimethylpyrazine, which corresponds to a concentrating of 0.108 percent (w/v), was added to the cell suspension (100 ml) with an optical density of 10. The p-xylene addition was stopped during the reaction of the substrate. Under these conditions, 1 mmol of 2,5-dimethylpyrazine over a period of 4 hours was converted to 0.9 mmol of 5-methyl-2-pyrazine carboxylic acid, corresponding to a yield of 90 percent, relative to the 2,5-dimethylpyrazine used.

EXAMPLE 4

*Pseudomonas putida* DSM 5709 was cultured analogously to Example 3 but with p-cymene as sole carbon source and energy source. After a period of 16 hours, 0.5 mmol of 5-methyl-2-pyrazine carboxylic acid was obtained, corresponding to a yield of 50 percent, relative to the 2,5-dimethylpyrazine used.

EXAMPLES 5 to 28

Examples 5 to 28 were performed according to Example 3 with an amount of 1 mmol of substrate per 100 ml of cell suspension and are summarized in Table 2.

TABLE 2

| Ex. | Substrate | Concentration of substrate in % (w/v) in the culture medium | Reaction Time in hours | End Product | Yield in % |
|---|---|---|---|---|---|
| 5 | 2-methyl pyrazine | 0.049 | 16 | 2-pyrazine carboxylic acid | 30 |
| 6 | 2,5-dimethyl-pyrazine | 0.108 | 4 | 2-methyl-5-pyrazine carboxylic acid | 90 |
| 7 | 2,6-dimethyl-pyrazine | 1.108 | 4 | 2-methyl-6-pyrazine carboxylic acid | 90 |
| 8 | 2,3,5-trimethyl-pyrazine | 0.122 | 16 | 2,3-dimethyl-5-pyrazine carboxylic acid | 50 |
| 9 | 2-chloro-3,6-dimethyl-pyrazine | 0.142 | 16 | 2-chloro-3 methyl-6-pyrazine carboxylic acid | 90 |
| 10 | 2-methyl-pyridine | 0.093 | 16 | 2-pyridine carboxylic acid | 90 |
| 11 | 3-methyl-pyridine | 0.093 | 16 | 3-pyridine carboxylic acid | 50 |
| 12 | 4-methyl-pyridine | 0.093 | 16 | 4-pyridine carboxylic acid | 30 |
| 13 | 2,6-dimethyl-pyridine | 0.107 | 16 | 6-methyl-2-pyridine carboxylic acid | 80 |
| 14 | 2,5-dimethyl-pyridine | 0.107 | 16 | 5-methyl-2-pyridine carboxylic acid | 40 |

TABLE 2-continued

| Ex. | Substrate | Concentration of substrate in % (w/v) in the culture medium | Reaction Time in hours | End Product | Yield in % |
|---|---|---|---|---|---|
| 15 | 2,4-dimethyl-pyridine | 0.107 | 16 | 4-methyl-2-pyridine carboxylic acid | 40 |
| 16 | 3,5-dimethyl-pyridine | 0.107 | 16 | 5-methyl-3-pyridine carboxylic acid | 40 |
| 17 | 6-chloro-2-methyl-pyridine | 0.128 | 16 | 6-chloro-2-pyridine carboxylic acid | 90 |
| 18 | 6-chloro 3-methyl-pyridine | 0.128 | 16 | 6-chloro-3-pyridine carboxylic acid | 90 |
| 19 | 2-chloro-3-ethyl-6-methyl-pyridine | 0.157 | 16 | 2-chloro-3-ethyl-6-pyridine carboxylic acid | 10 |
| 20 | 4,6-dimethyl-pyrimidine | 0.108 | 16 | 6-methyl-4-pyrimidine carboxylic acid | 20 |
| 21 | 3,5-dimethyl-pyrazole | 0.096 | 16 | 5-methyl-3-pyrazole carboxylic acid | 80 |
| 22 | 5-methyl-thiazole | 0.099 | 16 | 5-thiazole carboxylic acid | 80 |
| 23 | 4-methyl-thiazole | 0.099 | 16 | 4-thiazole carboxylic acid | 80 |
| 24 | 2,5-dimethyl-thiophene | 0.112 | 16 | 5-methyl-2-thiophene carboxylic acid | 90 |
| 25 | 2-methyl-thiophene | 0.098 | 16 | 2-thiophene carboxylic acid | 90 |
| 26 | 3-methyl-thiophene | 0.098 | 16 | 3-thiophene carboxylic acid | 90 |
| 27 | 2,5-dimethyl-furan | 0.096 | 16 | 5-methyl-2-furan carboxylic acid | 40 |
| 28 | 2,5-dimethyl-pyrrole | 0.095 | 16 | 5-methyl-2-pyrrole carboxylic acid | 40 |

EXAMPLE 5

Production of 5Methyl-2Pyrazine Carboxylic Acid

*Pseudomonas putida* ATCC 33015 was cultured in minimal medium, whose composition is indicated in Table 3 below, in a 20-liter bioreactor (2) at a working volume of 15 liters. The temperature was 30° C.; the pH was kept constant at 7.0 by the addition of potassium hydroxide. The gassing rate was 20 liters per minute. A mixture of 4 parts (v/v) of p-xylene and 1 part of 2,5-dimethylpyrazine served as the growth substrate. Feeding of this mixture into bioreactor (2) took place by pump (1). The addition of the growth substrate was coupled to a control (5) by a xylene measurement (4) in bioreactor exhaust air (3). Thus, by means of control (5), the xylene concentration in exhaust air (3) was kept constant at a value of 0.2 mmol/l. The biotransformation was stopped only when no more growth could be detected. FIG. 2 shows the results of such a biotransformation. Curve A of FIG. 2 represents the optical density at 650 nm. Curve B of FIG. 2 represents the concentration in g/l of 2,5-dimethylpyrazine. Curve C of FIG. 2 represents the concentration in g/l of potassium salt of 5-methyl-2-pyrazine carboxylic acid. With this technology, 5-methyl-2-pyrazine carboxylic concentrations of 38 g/k were obtained.

TABLE 3

| Ingredients | Amounts |
|---|---|
| Medium composition: | |
| $MgCl_2.6H_2O$ | 0.8 g/l |
| $CaCl_2$ | 0.16 g/l |
| $(NH_4)SO_4$ | 2 g/l |
| $NH_4Cl$ | 5 g/l |
| $Na_2SO_4$ | 0.25 g/l |
| $KH_2SO_4$ | 0.4 g/l |
| $Na_2HPO_4$ | 0.9 g/l |
| Trace elements | 1 ml/l |
| FeEDTA | 15 ml/l |
| Composition of the trace element solution: | |
| KOH | 15 g/l |
| $EDTANa_2.2H_2O$ | 10 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.2 g/l |
| Composition of FeEDTA: | |
| $EDTANa_2.2H_2O$ | 5 g/l |
| $FeSO_4.7H_2O$ | 2 g/l |

COMPARISON EXAMPLES (A) *Pseudomonal putida* ATCC 33015

The biotransformation of 3-methylpyridine with *Pseudomonas putida* ATCC 33015 was performed according to Example 3 with 1 mmol of 3-methylpyridine. After an incubation period of 8 hours, 0.25 mmol of nicotinic acid corresponding to a yield of 25 percent, relative to 3-methylpyridine used, was obtained.

(B) *Rhodoccocus rhodochrous* or Nocardia

*Rhodoccocus rhodochrous* DSM 43002 (ATCC 19149) was cultured in mineral medium according to Example 3 of 0.4 percent dodecane as the carbon source and the energy source and then washed in the same mineral medium, but without dodecane. The cell suspensions (100 ml) with an optical density at 650 nm of 10 were mixed in three separate flasks with the following compounds:

(a) 1 mmol of 3-methylpyridine, (b) 1 mmol of 3-methylpyridine and 0.055 mmol of dodecane, and (c) 1 mmol of 3-methylpyridine and 5.5 mmol of dodecane.

After 8 hours of incubation time at 30° C., nicotinic acid could not be detected in any of the batches.

What is claimed is:

1. Microbiological process for the oxidation of a methyl group in an aromatic 5- or 6-member ring heterocycle, the heterocycle exhibiting no substituent on the carbon atom adjacent to the methyl group to be oxidized to the corresponding carboxylic acid, characterized in that the methylated heterocycle is used as the substrate for the oxidation reaction and the oxidation reaction is performed by a microorganism of the genus Pseudomonas which utilizes xylene or cymene, the enzymes the microorganism having been previously induced by contact with an inducer which is in gaseous form, the inducer having been p-xylene, m-xylene, p-cymene, m-cymene, toluene, a benzyl alcohol, p-chlorobenzene, a monosubstituted or disubstituted methyl toluene, a monosubstituted or disubstituted ethyl toluene, or a monosubstituted or disubstituted chlorotoluene, the enzyme induction having been performed either with a compound, which serves the microorganism as the carbon source and the energy source, or with a compound, which does not serve the microorganism as the carbon source and the energy source, the microorganism of the genus Pseudomonas being a xylene-utilizing microorganism strain *Pseudomonas putida* with the designation ATCC 33015 or an effective mutant of said strain ATCC 33015, or cymene-utilizing microorganism strain *Pseudomonas putida* with the designation DSM 5709 or an effective mutant of said strain DSM 5709.

2. Process as claimed in claim 1 wherein the inducer is p-xylene, m-xylene, p-cymene or m-cymene.

3. Process as claimed in claim 1 wherein the reaction is performed with the xylene-utilizing microorganism strain *Pseudomonas putida* with the designation ATCC 33015 or an effective mutant of said strain.

4. Process as claimed in claim 1 wherein the reaction is performed with the cymene-utilizing microorganism strain *Pseudomonas putida* with the designation DSM 5709 or an effective mutant of said strain.

5. Process as claimed in claim 1 wherein the reaction is performed at a pH of 4 to 11.

6. Process as claimed in claim 1 wherein the reaction is performed at a temperature of 15° C. to 50° C.

7. Process as claimed in claim 1 wherein the reaction is performed with a methylated aromatic 5-member ring heterocycle, as the substrate which contains one or more heteroatoms from the group consisting of oxygen, nitrogen and sulfur.

8. Process as claimed in claim 1 wherein the reaction is performed with a methylated aromatic 6-member ring heterocycle, as the substrate, which contains one or more nitrogen atoms as the heteroatom.

9. Process as claimed in claim 1 wherein the enzyme inducer and/or the methylated heterocycle is fed as the substrate into a bioreactor, and the amount of the feed is regulated by the concentration of the enzyme inducer in the exhaust air of the bioreactor.

10. Process as claimed in claim 1 wherein the reaction takes place either with a single or continuous substrate addition so that the substrate concentration in the culture medium does not exceed 20 percent (w/v).

11. Process as claimed in claim 10 wherein the reaction is performed at a pH of 4 to 11.

12. Process as claimed in claim 11 wherein the reaction is performed at a temperature of 15° to 50° C.

13. Process as claimed in claim 12 wherein the reaction is performed with a methylated aromatic 5-member ring heterocycle, as the substrate, which contains one or more heteroatoms from the group consisting of oxygen, nitrogen and sulfur.

14. Process as claimed in claim 13, wherein the reaction is performed with a methylated thiophene, methylated furan, methylated pyrrole, methylated thiozole, methylated pyrazole or methylated imidazole as the substrate.

15. Process as claimed in claim 12 wherein the reaction is performed with a methylated aromatic 6-member ring heterocycle, as the substrate, which contains one or more nitrogen atoms as the heteroatom.

16. Process as claimed in claim 15 wherein the reaction is performed with a methylated pyridine, methylated pyrimidine, methylated pyrazine or with a methylated pyridazine as the substrate.

17. Process as claimed in claim 16 wherein the enzyme inducer and/or the methylated heterocycle is fed as the substrate into a bioreactor, and the amount of the feed is regulated by the concentration of the enzyme inducer in the exhaust air of the bioreactor.

18. Process as claimed in claim 17 wherein the concentration of the enzyme inducer is measured in the exhaust air with a measuring device and the amount of feed of the enzyme inducer and/or of the methylated heterocycle is regulated by a control, which is coupled to a measuring device.

19. Process according to claim 18 wherein the regulation takes place so that the concentration of the enzyme inducer in the exhaust air is kept constant and is between 0.001 and 10 mmol/l of exhaust air.

* * * * *